(12) United States Patent
Woodford et al.

(10) Patent No.: US 6,470,208 B1
(45) Date of Patent: Oct. 22, 2002

(54) METHOD AND APPARATUS FOR CONTROLLING X-RAY EXPOSURE DURING GATED CARDIAC SCANNING

(75) Inventors: Mark E. Woodford, Waukesha, WI (US); Kishore C. Acharya, Brookfield, WI (US); Steven J. Woloschek, Franklin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/474,962

(22) Filed: Dec. 30, 1999

Related U.S. Application Data

(60) Provisional application No. 60/166,466, filed on Nov. 19, 1999.

(51) Int. Cl.[7] .................................................. A61B 5/00
(52) U.S. Cl. .............................. 600/428; 378/8; 378/95
(58) Field of Search .............................. 600/413, 414, 600/425, 427, 428; 378/4, 8, 95; 250/363.04

(56) References Cited

U.S. PATENT DOCUMENTS

| 4,382,184 | A | * | 5/1983 | Wernikoff |
| 4,547,892 | A | * | 10/1985 | Richey et al. |
| 5,803,914 | A | * | 9/1998 | Ryals et al. ................. 600/407 |
| 6,068,595 | A | * | 5/2000 | Miyazaki et al. ........... 600/410 |
| 6,195,408 | B1 | * | 2/2001 | Acharya et al. |

* cited by examiner

*Primary Examiner*—Ruth S. Smith
(74) *Attorney, Agent, or Firm*—Carl B. Horton, Esq.; Armstrong Teasdale LLP

(57) ABSTRACT

A method is described for controlling x-ray exposure during gated cardiac scanning, including the steps of detecting a first cardiac signal; starting scanning after a pre-selected wait time after detecting the first cardiac signal; and stopping the scanning after a first to occur of passage of a pre-selected data collection time and detection of a second cardiac signal.

22 Claims, 2 Drawing Sheets

METHOD AND APPARATUS FOR CONTROLLING X-RAY EXPOSURE DURING GATED CARDIAC SCANNING

CROSS REFERENCE TO RELATED APPLICATIONS

This application claims the benefit of United States Provisional Application Ser. No. 60/166,466, filed Nov. 19, 1999.

BACKGROUND OF THE INVENTION

This invention relates generally to computed tomography (CT) imaging and, more particularly, to methods and apparatus for controlling x-ray exposure during gated cardiac scanning.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Methods are known for controlling patient exposure to x-rays during gated cardiac scanning. For example, it is known to control patient exposure based upon a prediction of when a heartbeat will occur. Heartbeat timing predictions often are inaccurate, and resulting image quality can be degraded by unpredicted cardiac motion. It would be desirable to provide a method for controlling x-ray exposure during cardiac scanning without sacrificing image quality. It also would be desirable to control patient exposure while scanning patients having irregular heart rates.

BRIEF SUMMARY OF THE INVENTION

There is therefore provided, in one embodiment, a method for controlling x-ray exposure during gated cardiac scanning, including the steps of detecting a first cardiac signal; starting scanning after a pre-selected wait time after detecting the first cardiac signal; and stopping the scanning after a first to occur of passage of a pre-selected data collection time and detection of a second cardiac signal. The above-described method allows scanning exposure to be controlled for patients having heart rates as high as 92 beats per minute without sacrificing image quality for patients having slower heart rates.

DETAILED DESCRIPTION OF THE INVENTION

Figure 1:
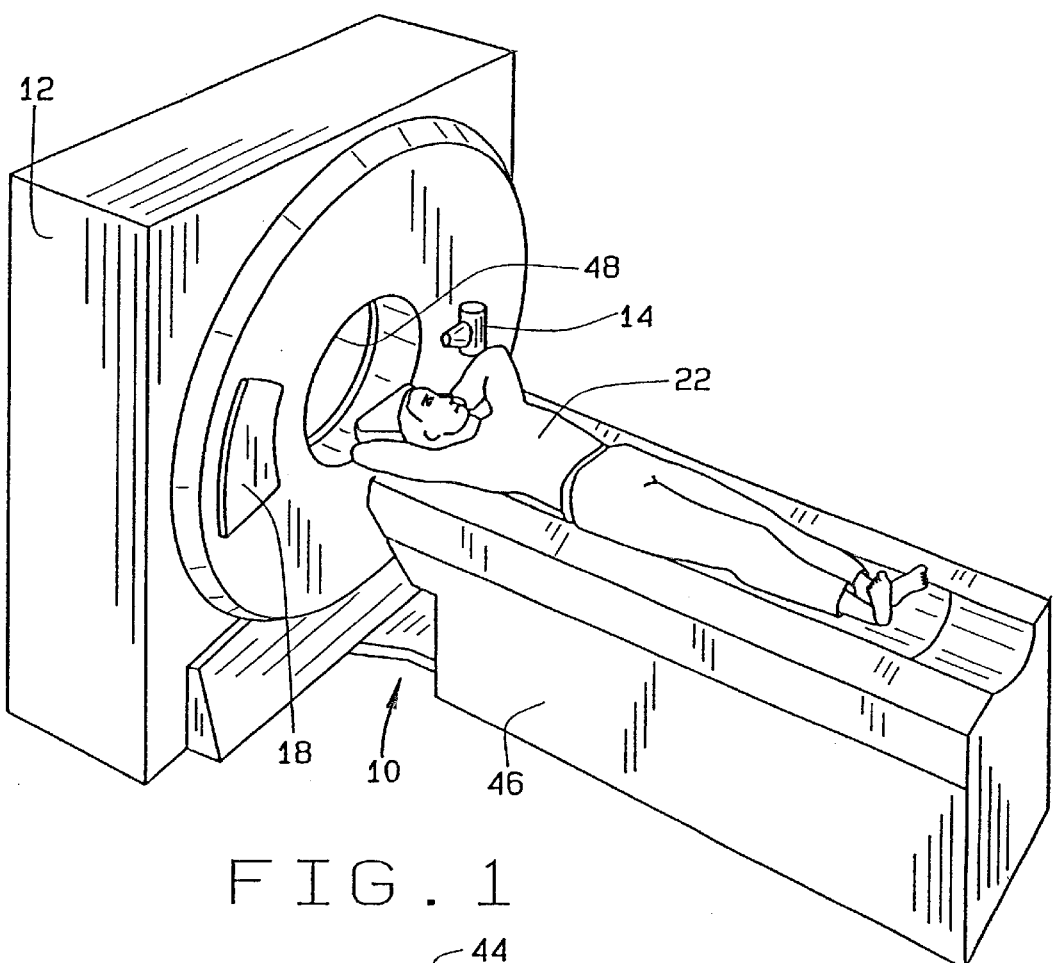
FIG. 1 is a pictorial view of a CT imaging system.
Figure 2:
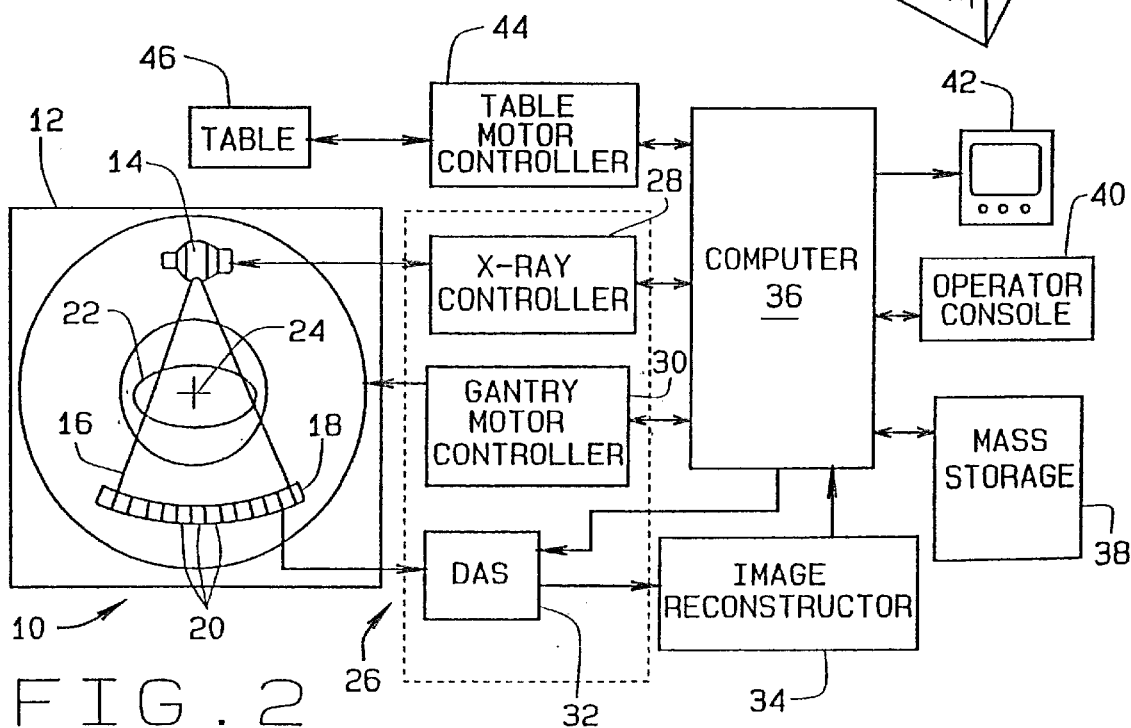
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14, for example an x-ray tube, that projects a beam of x-rays 16 toward a detector array 18 on the opposite side of gantry 12. Detector array 18 is formed by detector elements 20 that together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that receives cardiac signals from patient 22 and provides power and timing signals to x-ray source 14. Control mechanism 26 also includes a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38.

Computer 36 also receives commands and scanning parameters from an operator (not shown) via console 40 that has a keyboard. An associated cathode ray tube display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

Figure 3:
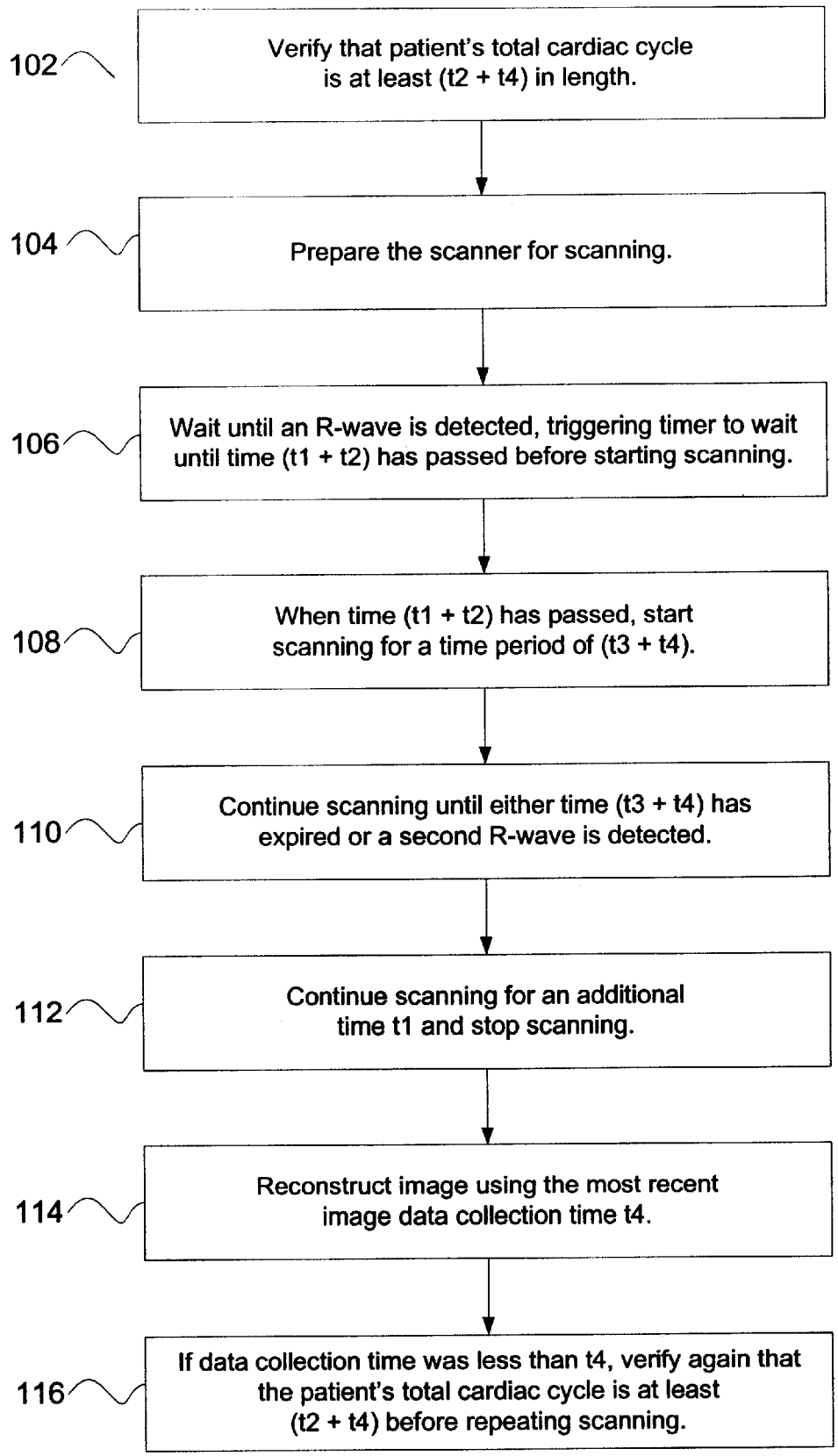
FIG. 3 is a flow diagram of an embodiment of a method for controlling x-ray exposure of the present invention.

Referring to FIG. 3, a method for controlling x-ray exposure during gated cardiac scanning includes verifying 102 that patient 22 has a total cardiac cycle at least as long as a time (t2+t4). Time t2 is a time pre-selected as sufficient for completion of cardiac systolic motion, e. g. approximately 150 milliseconds. Time t4 is a pre-selected minimum image data collection time required for imaging by system 10, e. g. 500 milliseconds. After verification, imaging system 10 is prepared for scanning 104 and is set to wait 106 for a first cardiac signal, for example, an R-wave signal, from patient 22. Detection of an R-wave signal sets a timer 106 to start scanning after a pre-selected wait time (t1+t2), where time t1 is a pre-selected time from R-wave detection through cardiac contraction start, e. g. approximately 50 milliseconds.

After wait time (t1+t2) has passed, scanning is started 108 and is timed to continue through a pre-selected data collection time (t3+t4), where time t3 is a pre-selected time estimated for completion of cardiac fast filling, e. g. approximately 250 milliseconds. Scanning continues 110 either until data collection time (t3+t4) has passed or until a second cardiac signal is detected, for example, a second R-wave signal. Occurrence of either event results in a continuation of scanning 112 for an additional time t1.

After additional time t1 has passed, scanning is stopped 112. If data was collected over at least a minimum image data collection time t4 ending at the conclusion of scanning, an image is reconstructed 114 using data collected over the most recent minimum image data collection time t4. If, for example, either of first or second cardiac signals was triggered by an irregular heartbeat, time over which data was collected may be less than minimum image data collection time t4. In this case, before repeating scanning, it may be advisable to verify again 116 that patient 22 total cardiac cycle is at least (t2+t4) milliseconds long so that data sufficient for reconstructing an image can be collected.

The above-described method does not require a prediction of patient heart rate but uses a patient cardiac signal, e.g. an R-peak signal, to start scanning after a wait time selected to avoid scanning during most of cardiac motion associated with systole. By avoiding scanning during these times, the above-described method reduces x-ray exposure while scanning patients having irregular heart rates. Exposure also is controlled for patients having a cardiac cycle as fast as (t2+t4), i. e. time for systolic motion completion plus minimum data collection time required for system 10 image reconstruction. Thus, for example, where (t2+t4) is 650 milliseconds, x-ray exposure is controlled for patients having heart rates as high as 92 beats per minute.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other imaging systems, including "fourth generation" CT systems wherein the detector is a full-ring stationary detector and only the x-ray source rotates with the gantry, may be used. Moreover, the system described herein performs an axial scan; however, the invention may be used with a helical scan although more than 360 degrees of data are required. While the invention has been described in terms of various specific embodiments, those skilled in the art will recognize that the invention can be practiced with modification within the spirit and scope of the claims.

What is claimed is:

1. A method for performing gated cardiac scanning using an imaging system, said method comprising the steps of:
   detecting a first cardiac signal;
   starting scanning after a pre-selected wait time after detecting the first cardiac signal, wherein the pre-selected wait time is selected in accordance with (t1+t2) where t1 represents a pre-selected time from R-wave detection through cardiac contraction start and t2 represents a pre-selected time for completing systolic motion; and
   stopping the scanning after at least one of a passage of a pre-selected data collection time and a detection of a second cardiac signal.

2. A method in accordance with claim 1 wherein the step of detecting a first cardiac signal comprises detecting an R-wave signal.

3. A method in accordance with claim 1 wherein t1 is approximately 50 milliseconds and t2 is approximately 150 milliseconds.

4. A method in accordance with claim 1 wherein the scanning is stopped a pre-selected additional time after the first to occur of passage of a pre-selected data collection time and detection of a second cardiac signal.

5. A method in accordance with claim 4 further comprising the step of pre-selecting the data collection time in accordance with (t3+t4) where t3 represents a pre-selected time to complete cardiac fast filling and t4 represents a pre-selected minimum image data collection time.

6. A method in accordance with claim 5 wherein t3 is approximately 250 milliseconds and t4 is approximately 500 milliseconds.

7. A method in accordance with claim 6 wherein the second cardiac signal is an R-wave signal.

8. A method in accordance with claim 5 further comprising the step of reconstructing an image using data collected over the minimum image data collection time preceding the ending of the scanning.

9. A method in accordance with claim 4 further comprising the step of pre-selecting the additional time as a time from R-wave detection through cardiac contraction start.

10. A method in accordance with claim 9 comprising the step of pre-selecting the additional time as approximately 50 milliseconds.

11. A method in accordance with claim 1 further comprising the step of verifying a minimum cardiac cycle in accordance with (t2+t4) where t2 represents a pre-selected time for completing systolic motion and t4 represents a pre-selected minimum image data collection time.

12. An imaging system for performing gated cardiac scanning, said system comprising:
   a radiation source;
   a detector array positioned to receive x-rays from said x-ray source; and
   an x-ray controller coupled to said radiation source, said x-ray controller configured to:
   detect a first cardiac signal;
   start scanning after a pre-selected wait time after detecting the first cardiac signal, wherein the pre-selected wait time is selected in accordance with (t1+t2) where t1 represents a pre-selected time from R-wave detection through cardiac contraction start and t2 represents a pre-selected time for completing systolic motion; and
   stop the scanning after at least one of a passage of a pre-selected data collection time and a detection of a second cardiac signal.

13. A system in accordance with claim 12 wherein to detect a first cardiac signal, said x-ray controller further configured to detect an R-wave signal.

14. A system in accordance with claim 13 wherein t1 is approximately 50 milliseconds and t2 is approximately 150 milliseconds.

15. A system in accordance with claim 12 wherein said x-ray controller is further configured to stop the scanning a pre-selected additional time after the first to occur of passage of a pre-selected data collection time and detection of a second cardiac signal.

16. A system in accordance with claim 15 wherein said x-ray controller further configured to pre-select the data collection time in accordance with (t3+t4) where t3 represents a pre-selected time to complete cardiac fast filling and t4 represents a pre-selected minimum image data collection time.

17. A system in accordance with claim 16 wherein t3 is approximately 250 milliseconds and t4 is approximately 500 milliseconds.

18. A system in accordance with claim 12 wherein the second cardiac signal is an R-wave signal.

19. A system in accordance with claim 16 wherein said x-ray controller further configured to reconstruct an image using data collected over the minimum image data collection time preceding the ending of the scanning.

20. A system in accordance with claim 15 wherein said x-ray controller further configured to pre-select the additional time as a time from R-wave detection through cardiac contraction start.

21. A system in accordance with claim 20 wherein said x-ray controller further configured to pre-select the additional time as approximately 50 milliseconds.

22. A system in accordance with claim 12 wherein said x-ray controller further configured to verify a minimum cardiac cycle in accordance with (t2+t4) where t2 represents a pre-selected time for completing systolic motion and t4 represents a pre-selected minimum image data collection time.

* * * * *